United States Patent [19]
Garner

[11] Patent Number: 6,160,618
[45] Date of Patent: Dec. 12, 2000

[54] HYPERSPECTRAL SLIDE READER

[75] Inventor: Harold R. Garner, Flower Mound, Tex.

[73] Assignee: Board of Regents, The University of Texas System, Austin, Tex.

[21] Appl. No.: 09/335,215

[22] Filed: Jun. 17, 1999

Related U.S. Application Data

[60] Provisional application No. 60/089,960, Jun. 19, 1998.

[51] Int. Cl.[7] .................................................. G01N 21/64
[52] U.S. Cl. ...................... 356/318; 356/328; 250/458.1; 250/461.1
[58] Field of Search .................................. 356/305, 326, 356/328, 317, 318, 417; 250/458.1, 459.1, 461.1, 461.2

[56] References Cited

U.S. PATENT DOCUMENTS

| | | | |
|---|---|---|---|
| 5,539,517 | 7/1996 | Cabib et al. | 356/346 |
| 5,782,770 | 7/1998 | Mooradian et al. | 600/476 |
| 5,784,162 | 7/1998 | Cabib et al. | 356/346 |
| 5,817,462 | 10/1998 | Garini et al. | 435/6 |

OTHER PUBLICATIONS

Glenn H. McGall, Anthony D. Barone, Martin Diggelmann, Stephen P.A. Fodor, Erik Gentalen and Nam Ngo, "The Efficiency of Light–Directed Synthesis of DNA Arrays on Glass Substrates," Journal of the American Chemical Society, Jun. 4, 1997, pp. 5081–5090.

Ann Cavini Pease, Dennis Solas, Edward J. Sullivan, Maureen T. Cronin, Christopher P. Holmes and Stephen P.A. Fodor, "Light–Generated Oligonucleotide Arrays for Rapid DNA Sequence Analysis," Proc. Natl. Acad. Sci. USA, vol. 91, May 1994, pp. 5022–5026.

Kevin M. O'Brien, Jonathan Wren, Varshal K. Dave, Dian Bai, Richard D. Anderson, Simon Rayner, Glen A. Evans, Ali E. Dabiri and Harold R. Garner, "ASTRAL, A Hyperspectral Imaging DNA Sequencer," Review of Scientific Instruments, vol. 69, No. 5, May 1998, pp. 1–6.

Glenn McGall, Jeff Labadie, Phil Brock, Greg Wallraff, Tiffany Nguyen and William Hinsberg, "Light–Directed Synthesis of High–Density Oligonucleotide Arrays Using Semiconductor Photoresists," Proc. Natl. Acad. Sci. USA., vol. 93, Nov. 1996, pp. 13555–13560.

Tom Strachan, Marc Abitbol, Duncan Davidson and Jacques S. Beckmann, "A New Dimension for the Human Genome Project: Towards Comprehensive Expression Maps." Nature Genetics, vol. 16, Jun. 1997, pp. 126–132.

Steven A. Sundberg, Ronald W. Barrett, Michael Pirrung, Amy L. Lu, Benjang Kiangsoontra and Christopher P. Holmes, "Spatially–Addressable Immobilization of Macromolecules on Solid Supports," J. Am. Chem. Soc. 1995, pp. 12050–12057.

William Feldman and Pavel Pevzner, "Gray Code Masks for Sequencing by Hybridization," Genomics, 1994, pp. 233–235.

Linda A. Chrisey, C. Elizabeth O'Ferrall, Barry J. Spargo, Charles S. Dulcey and Jeffrey M. Calvert, "Fabrication of Patterened DNA Surfaces," Nucleic Acids Research, 1996, vol. 24, No. 15, pp. 3040–3047.

Jay T. Groves, Nick Ulman and Steven G. Boxer, "Micropatterning Fluid Lipid Bilayers on Solid Supports," Science, vol. 275, Jan. 31, 1997, pp. 651–653.

(List continued on next page.)

*Primary Examiner*—F. L. Evans
*Attorney, Agent, or Firm*—Edwin S. Flores; Gardere & Wynne, L.L.P.

[57] ABSTRACT

An apparatus and method for analyzing samples on a slide comprising a slide mover positioned to hold a slide, a imaging spectrometer positioned in the path of light from the slide to split the light line into a light array, a light amplifier may be positioned between the imaging spectrometer and a camera, is disclosed. The camera can detect the entire spectrum of light produced by the imaging spectrometer.

54 Claims, 5 Drawing Sheets

OTHER PUBLICATIONS

Miri Park, Christopher Harrison, Paul M. Chaikin, Richard A. Register and Douglas H. Adamson, "Block Copolymer Lithography: Periodic Arrays of 1011 Holes in 1 Square Centimeter," Science, vol. 276, May 30, 1997, pp. 1401–1404.

Enoch Kim, Younan Xia and George M. Whitesides, "Polymer Microstructures Formed by Moulding in Capillaries," Nature, vol. 376, Aug. 17, 1995, pp. 581–584.

Larry J. Hornbeck, Digital Light Processing for High–Brightness, High–Resolution Applications, Texas Instruments Incorporated, pp. 1–14.

HYPERSPECTRAL SLIDE READER

This application claims the benefit under 35 U.S.C. §119(e) of any U.S. Provisional Application Serial No. 60/089,960, filed Jun. 19, 1998.

This invention was made with government support under National Institutes of Health Grant No. RO1-CA-7811-01. The government has certain rights in the invention.

TECHNICAL FIELD OF THE INVENTION

The present invention relates in general to the field of biological sample analysis, and more particularly, to an apparatus and method for scanning a slide using the entire spectrum of light, concurrently and in real time.

BACKGROUND OF THE INVENTION

Without limiting the scope of the invention, its background is described in connection with the analysis of nucleic acid, amino acid, small molecular and/or cellular samples, as an example.

Heretofore, in this field, the analysis of biologically relevant samples has been accomplished using techniques that detect the presence of a marker or markers in known and unknown samples. To detect the presence of these markers, techniques such as, e.g., radiolabelling, fluorescence or enzymatic labeling, have been used to detect the presence or absence of binding between a component of the sample and a substrate or matrix on which the appropriate binding group or ligand has been immobilized.

Such systems are described in U.S. Pat. No. 5,817,462, which issued to Garini, et al., and U.S. Pat. No. 5,539,517 issued to Cabib, et al., in which interferometric dispersal and recombination of collimated light is used to detect a light signal. The systems described, however, uses discrete filtering system to detect individual samples. Also, these samples are read with discrete filtering elements that prevent the detection of fluorochromes that have adjacent wavelengths of exitation or transmission.

One such system is described in U.S. Pat. No. 5,744,305, which issued to Fodor, et al., in which a synthetic strategy for creating large scale chemical diversity in an array is described. Solid-phase chemistry, photolabile protecting groups and photolithography are used to obtain a light directed spatially-addressable parallel chemical synthesis. Using binary masking techniques, a reactor system is used that can be used to improve data handling and collection. The system described, however, uses a single light source to detect individual samples. Also, these samples are read only once for full spectral coverage, greatly increasing the throughput time of the system.

Another system and method of detection of samples is described in U.S. Pat. No. 5,424,186 issued to Fodor, et al. A method for synthesizing oligonucleotides on a solid substrate is described. The substrate used in the device described provides for the incorporation of semiconductor structures that are used to detect binding of samples to an array of ligands on the surface of the semiconductor. This "biochip" has been the subject of much attention in the art (See e.g., To Affinity . . . and Beyond, Nature Genetics, Vol. 14, 367–370, 1996). The system, however, is only useful for the detection of the material permanently attached to the surface of the chip. The system also requires an expensive customized reader to provide a limited output.

Yet another system involves the production or arrays on slides by deposition and attachment of DNA or other biological/chemical sample. This array is then interrogated with photolabile unknown samples (DNA, RNA, other biological/chemical) and quantitative detection is done using a fluorescent or chemiluminescent reader. Current readers use filter systems to select the desired light, thus limiting the number and accuracy of the unknown samples being measured.

SUMMARY OF THE INVENTION

It has been found, however, that present apparatus and methods fail to meet the demand for a low cost, efficient, customizable slide reader that is capable of overlapping, concurrent data acquisition and analysis over the entire spectrum of light. A problem found in alternative systems is that they are only capable of scanning one or two samples per slide, due to the use of single or dual wavelength detection. Another problem with present systems is that scanning is done in two dimensions, which increases the time required for data aquisition.

The present invention is an apparatus for reading sample fluorescence on a slide comprising, a slide mover positioned to hold a slide in the path of the light line. An imaging spectrograph, is positioned to disperse light emitted from the slide into a light spectrum. Following the interaction of the light line with the samples on the slide, a camera detects the light spectrum produced by the light dispersive element to determine the sample fluorescence. The type and extent of sample fluorescence is used to determine with what type of fluorescent labeling the sample has interacted to produce a light array. The camera may be, e.g., a CCD camera. A light amplifier, such as a microchannel plate amplifier, may be placed between the light dispersive element and the camera to amplify light emitted from samples on the slide. The slide reader may also include at least one light source and a light line generator that is positioned to spread light into a light line prior to interaction with samples on the slide. By light generated from the slide it is meant that light detected by the camera from the slide may be produced from a reaction on the slide (e.g., a chemiluminescent reaction) or from light that is produced by a light source that interacts with a sample on the slide, wherein the sample emits light at the same or a different wavelength along the entire spectrum of light. Detection by the camera may be along a line of samples along a slide, whether in the X direction, Y direction or diagonally.

The light source of the invention may be a laser, a lamp, or a combination of both. Examples of lasers include an argon ion laser, or a diode-pumped solid state laser, or a helium-neon laser or a combination thereof. Lamps for use with the invention may be a broadband ultraviolet lamp, or a mercury lamp, or a zenon lamp, or combinations thereof. In one embodiment of the present invention the light may be further defined as comprising a continuum or spectrum of light. A light dispersive element for use with the present invention is, for example, an imaging spectrograph which does not depend on interferometric dispersal and recombination of light for its function. Also, an astigmatism correcting lens may be positioned between the slide and the imaging spectrograph. The slide mover may be a linear motion drive slide mount. Furthermore, the light source selected will depend on the fluorochrome that is used to stain samples on the slide. The hyperspectral slide reader can further comprise a data acquisition system or computer connected to the camera. The data acquisition system or computer may store the data for further analysis, compute results based on the input acquired by the camera directly or indirectly, or both.

The apparatus may also include a variable spectral filter positioned between the light source and the sample. The slide mover may be a linear motion drive slide mount. The variable spectral filter may be positioned on, and its position controlled by a slide mover, which may also be under control of the computer. In one embodiment the variable spectral filter is a linear variable spectral slide filter. One or more variable spectral filters may be used in series, before or after the sample, and before the imaging spectrometer to fine-tune the light that strikes the sample, or that is emitted by the sample. Furthermore, the one or more variable spectral filters may be swept across the light source (be it the sample itself or light emitted by light source) in a time-dependent manner to take discrete wavelength measurements over time.

A light amplification device, such as a micro channel plate amplifier, may be placed between the imaging spectrometer and the camera to improve the sensitivity of this system. The present invention also includes a method of scanning samples on a slide in multiple wavelengths comprising the steps of, generating one or more wavelengths of light as a light line, illuminating at least one sample with the light line, splitting the light line into a two dimensional array of light, amplifying the array of light using a microchannel plate light amplifier, and detecting the two dimensional array of light.

The present invention may also be used as a chemiluminescent detection system, for detection or emitted light without illumination by a light source. Chemiluminescence may be intrinsic to the sample disposed on the slide, or may be added during the staining of the sample.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

Figure 1:
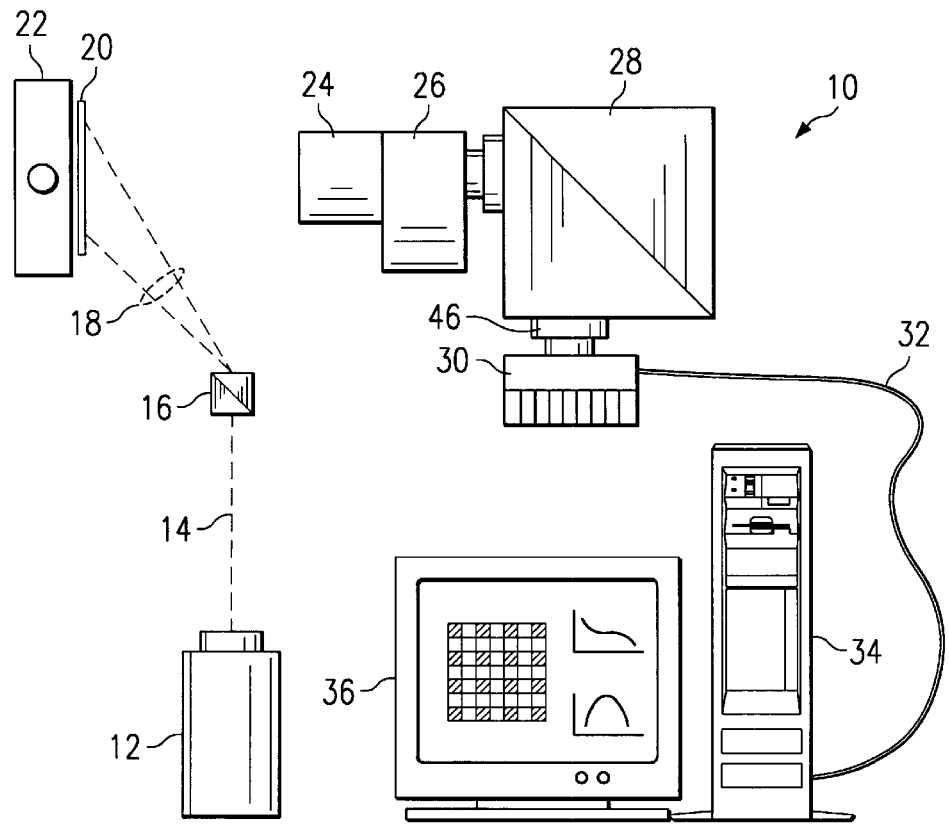
FIG. 1 is a diagram of the basic physical components of a hyperspectral slide reader with independent illumination and detection.

While the making and using of various embodiments of the present invention are discussed in detail below, it should be appreciated that the present invention provides many applicable inventive concepts which may be embodied in a wide variety of specific contexts. The specific embodiments discussed herein are merely illustrative of specific ways to make and use the invention and do not delimit the scope of the invention.

A hyperspectral image is one that is fully three dimensional, that is, an X-Y spatial image at an arbitrarily large number of wavelengths. The individual signature of differing emitting bodies can then be separated giving a complete view and content of features. Hyperspectral imaging has traditionally been used for satellite and airborne imaging systems. Specifically, imaging spectrographs in satellites have been used for environmental analysis (LANDSAT, etc.), geological, oceanographic, and topographic imaging. From these images have come the much publicized data on deforestation, subterranean resources, and oceanographic changes and blooms.

Spectral decomposition is a mathematical/algorithmical process by which individual components (signatures, such as emission spectra of dyes) may be uniquely separated from a composite (full spectral) image knowing the signature of each component measured separately (dye emission spectra, for example). Normally, spectral decomposition is performed using a simple linear curve fitting routine, but occasionally, depending on the fitting functions and the data characteristics, single value decomposition or nonlinear approaches are necessary. All these algorithms (Levenberg-Marquardt method for example for nonlinear decomposition) are extensively used in data analysis. The hyperspectral slide reader is based on an epi-fluorescence or direct coupling optics arrangement, but with the spectral resolving component being an imaging spectrograph instead of filters. The hyperspectral slide reader produces, after software processing, a decomposition of the image from known/measured emission spectra of the dyes and a high spectral resolution representation of the data.

The hyperspectral slide reader of the present invention can scan, e.g., one slide at a time, with three lasers and full spectral coverage allowing for dye multiplexing up to an estimated depth of eight to about 12 simultaneous detection events on a single array. The hyperspectral slide reader has a dynamic range of 10,000, obtainable in increments of 4,096 by retuning the laser power to scan for high copy of low copy number hybridizations or chemiluminescence to the array. Alternatively, the dynamic range may be increased by using a camera with a larger dynamic range. Presently available commercial system, such as the STORM (Molecular Dynamics, U.S.A.), has a large dynamic range (1:100,000), but the disadvantages are single wavelength and cost. Other commercial systems include Affymetrix GeneChip readout system made by Hewlett Packard and the ScanArray 3000 by General Scanning, Inc.

FIG. 1 shows one embodiment of a hyperspectral slide reader of the present invention, also referred to as a MAGNA reader, and is generally depicted as 10. The hyperspectral slide reader 10 can generally be described as a scanning fluorochrome or fluorescence and chemiluminescence slide reader. A light source, such as laser 12, produces a light beam 14 that is spread into a light line 18 by a light line generator 16. The light line 18 strikes a slide 20 that may be moved by a slide mover 22.

Alternatively, the light source 12 and light line generator 16 may not be necessary if the entire light generation process from the sample is based on chemiluminescence emitted from slide 20. Chemiluminescence for use with the invention may be, e.g., Lumigen-PPD or Lumi-Phos 530 (Boehringer Mannheim, U.S.A.), or AMPPD or CSPD (Tropix, U.S.A.).

A slide 20, may be moved in one or more dimensions past the light line 18, and the emission from the slide 20 is depicted as entering a lens 24. An imaging spectrometer 28, e.g., an imaging spectrometer, is used to spread emitted light that enters the lens 24 into a portion of, or the entire spectrum of, light. Once dispersed, a light amplifier 46, placed between the imaging spectrometer 28 and the camera 30, may be used to greatly improve the sensitivity of the system. The spectrum of light generated is reflected into a camera 30.

The output of the camera 30 may be sent to a computer 34 via a computer link 32. The computer 34 can store or process the data captured by the camera 30 to provide data processing and output. A display 36 may be used to display scan results in real-time. The computer 34 can store scan information for future analysis or to direct other automated systems based on the data gathered, stored or analyzed.

Alternatively, the slide 20 could be held in a single position and the light line 18 could be scanned past the samples on slide 20. Using the fixed slide 20 embodiment, however, would require that the light line 18 that emerges from the slide 20 be redirected into the detection system, by a lens 24 or other method. One such method would be to move the entire detector system to align with the light line 18 that is being scanned past the slide 20.

Using the hyperspectral slide reader 10 there are basically three dimensions of data that must be produced: X, Y, and wavelength. With the hyperspectral slide reader 10, the Y and wavelength information is taken simultaneously and is kept in a two dimensional image file. The slide 20 is moved in the X dimension past the laser/detector in small increments and at each step a file containing Y and wavelength is created. During or after the entire slide 20 is swept past the light line 18, and all files have been saved, the data from all the files may be merged into one large file using the custom software CHANGELING (available from GESTEC at Southwestern University Medical Center, Dallas, Tex.). The large file may be partially processed during its creation to make the data readable by other software and make it more biologically intuitive, e.g., by normalizing data and conducting background subtraction. The display 36 can show the data output as an image file, with X and Y viewable as a depicted as slide 20. The wavelength information may be processed by 'windowing' or 'spectral decomposition' to make the third dimension (intensity or color of the X-Y image) reflect the fluorescence emission for each dye label. From this point, additional software, e.g., IPLab, NIH Image, etc., can further process the data to extract the fluorescence or chemiluminescence intensity of each spot to create a table of data that may be related to, e.g., the expression level of a particular gene.

The system depicted is based on an imaging spectrometer 28 that may be an ARC imaging spectrograph. The camera 30 may be, e.g., a Photometrix cooled charge-coupled display (CCD) camera with a PCI bus interface. A lens system for use with the invention can include a standard 'C' mount camera lens, a dichroic mirror and/or a cylindrical lens. Light source 12 may be, e.g., an Argon Ion laser (488 nm and 514 nm lines), a solid state laser, a HeNe laser, or other lamp source. The line generator 16 may be, e.g., a prism that causes light entering the line generator 16, whether in the form of a beam of a combination of beams to form a light line 18. A cylindrical lens also may be used to focus a laser beam 14. Computer 34 may be, e.g., a Macintosh or PC computer that can store and process imaging data, as well as control the slide mover 22. The slide mover 22 may be, e.g., a Ludl X-Y microscope stage or a Scanalytics, Inc., U.S.A., precision motorized microscope stage interfaced directly to a computer 34. The slide stage is used to move the slide across the light line 14 that is being monitored by the optics detector. Software for use in the computer 32 can include IPLab software an/or 'C' software. To create a symmetric X-Y grid, 1536 pixel by 3 pixel or 4,608 total pixel hyperspectral image may be acquired. This size X-Y grid can produce up to 7,247,757,312 pixels per slide.

In one embodiment, specifications for the MAGNA hyperspectral slide 10 reader include a camera 30, having a 12 bit (4,096) depth, 1536 pixels in the Y dimension, 1024 pixels in wavelength. Pixels read by the camera 30 and forwarded to the computer 32, may be binned to reduce data or noise. In the case of the slide mover 22, specific directions for slide orientation may be, e.g., one inch in the Y dimension and 3 inches in the X dimension, when controlling the movement of a one by three inch slide 20. Initial hyperspectral files may be 1536 by 1024 pixels. Pixel density in the Y dimension may be 19 millimeters divided by 1536 pixels, giving a 12.4 micron resolution. Pixels across a spot in the Y dimension are calculated to be equal to 100 microns/12.4 microns per feature giving a total of 8 pixels per 100 micron width. Each step in the X dimension may be 12.4 microns, thereby matching the space measured in the Y dimension. By adjusting the magnification of the lens 24, arbitrary resolutions may be obtained by scanning subsets of the slide.

Movement of the slide in the X dimension can occur in increments per X-dimension step equal to about 12.4 microns, distance divided by 0.68 microns per increment, will require 18 increments per measurement. The final image captured having 1536 by 4608 by depth pixel, will be of approximately 15 megabytes per color or wavelength. One slide 20 may be concurrently scanned, however, further automation permits more than one slide to be scanned at a time using, e.g., one or more parallel processors, slide movers, light sources or combinations thereof. The wavelength coverage, namely, the center wavelength and range, are variable with present coverage from 480 nm to 700 nm, but may be adjusted depending on the fluorochrome and light source used.

One example of a light source can include several different lasers or lamps that have different power, such as: a 25 mW Argon laser, a 10 mW Diode pumped solid state laser and/or a 1 mW HeNe laser. These lasers are best seen in conjunction FIG. 2, in which these lasers are numbers 12a, 12b and 12c, respectively. These laser provide light having a wavelength of 488 nm, 514 nm, 532 nm, and 633 nm that contribute to the light line 18, which is formed by light line generator 18. Cylindrical lenses 40 are positioned to control the laser light and form a focus on the slide that may be confocal. The light line 18 is deflected into the slide 20 by a dichroic mirror 42. In this embodiment, the illumination provided by the light line 18 may be directed to the slide in either an epi-fluorescence arrangement (shown FIG. 2) or independently from the light collection optics, including illumination from above (shown in FIG. 1) or through the slide 20.

After wavelength dispersion, a light amplifier 46 may be used to improve system sensitivity. A microchannel plate amplifier, which is sensitive to all wavelengths as input and produces a monochromatic output, may be used because at this point wavelength information is preserved as it has been spread in space across the camera.

The integration time for the camera 30 capture may be from 0.01 to 5 seconds per X position. By using a light line 18 to concurrently scan all the samples in the Y dimension, for example, the present invention not only decreases processing time, but can do so using the entire spectrum of light. Furthermore, the use of a light line 18 generally eliminates one or the variables that contributes to poor readings, namely, movement of a laser beam in both the X and Y dimension. As the slide 20 is moved in the X dimension it allows for the use of higher precision slide moving 22 equipment. It also reduced the flutter or variance that may be observed in movers that are two directional. As precision in two dimensional slide movers 22 improves, however, those systems may be used as slide mover 22.

Using a one-directional slide mover 22, for example, scan times of 46 seconds to 380 minutes may be used depending on the desired sensitivity. Concurrent with, or following data capture, the data may be analyzed in approximately 20 minutes, if done off-line, using a Macintosh 9600/233. Data acquisition software used may be the IPLab software for the camera and slide mover drivers.

A number of fluorochromes may be used with the present invention. In fact, the hyperspectral slide reader 10 avoids the limits imposed by single or double wavelength light source devices by providing for the ability to capture images that are in essence a three-dimensional image of the slide, namely, position in the X dimension, position in the Y dimension and the third dimension representing the emission spectra. The three-dimensional analysis provided for herein, is accomplished using an astigmatism corrected imaging spectrograph interfaced to a light amplifier 46 and a cooled camera 30. The camera 30 can have 12 bits of dynamic range, and a 1536×1024 pixel spatial resolution. The imaging spectrometer 28 separates a one-dimensional (line) image of an object into various wavelengths into a second dimension. By scanning the object in one dimension a full two-dimensional image is created, but with all wavelength information preserved. One advantage of the hyperspectral slide reader 10 of the present invention is that the entire emission spectra is taken, therefore, a large number of nucleotide fluorochromes may be used simultaneously, for example, at least 6 and up to about 12.

Sequencing fluorochromes, e.g., FAM, JOE, TAMRA, and ROX, available from Applied Biosystems Incorporated, U.S.A., or other recently developed dyes and energy transfer dyes may be used. The slide 20 may be illuminated using a 40 mW Argon ion laser (488 and 514 nanometer), which has been run through a light line generator 16 to diffuse it in one dimension. The diffused light line 18 is directed to the slide 20, that is also viewed by the imaging spectrometer 28, light amplifier 46 and camera 30. The slide 20 is mounted to a linear motion drive, or slide mover 20, so that the light line 18 moves across the slide 20, and at each position a spectral image (one spatial dimension and one spectral dimension) is taken. After the scan is complete, the spectral information may be deduced from the image cube (FIG. 3), giving two-dimensional information for each fluorochrome (FIG. 4). Because the spectral information is decomposed computationally, dyes with broad emission spectra peaks that are close or overlapping may be differentiated. Furthermore, because the entire spectra is taken, there are more photons acquired in comparison to filter-based system, giving a sensitivity increase of about five to ten.

Fluorochromes or dyes for use with the present invention will depend on wavelength and coupling structure compatibility. By means of example, Fluorescein-5-EX, 5-SFX, Rhodamine Green-X, Bodipy FL-X, Cy2-OSu, Fluor X, 5(6)TAMRA-X, Bodipy TMR-X, Rhodamine Red-X, Texas Red-X, Bodipy TR-X, Cy3-OSu, Cy3.5-OSu, Cy5-Osu and/or Cy5.5-OSu, may be used if desired.

Figure 3:
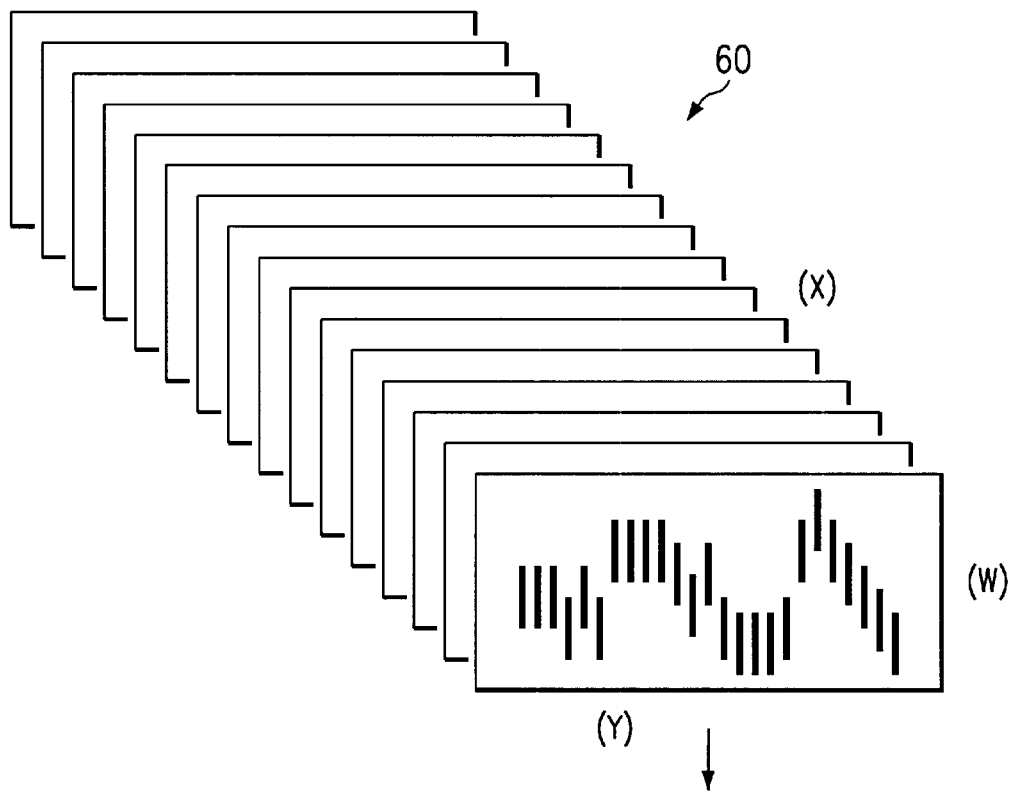
FIG. 3 is a diagram that represents images captured by a hyperspectral slide reader as disclosed herein.
Figure 4:
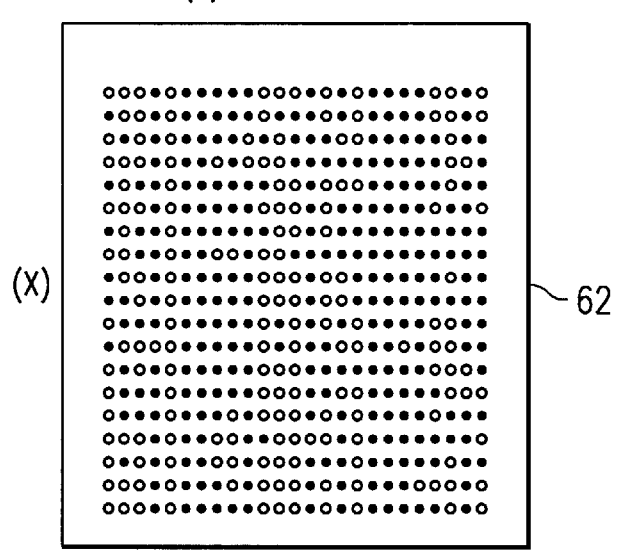
FIG. 4 is a representation of a compiled hyperspectral slide.
Figure 5:
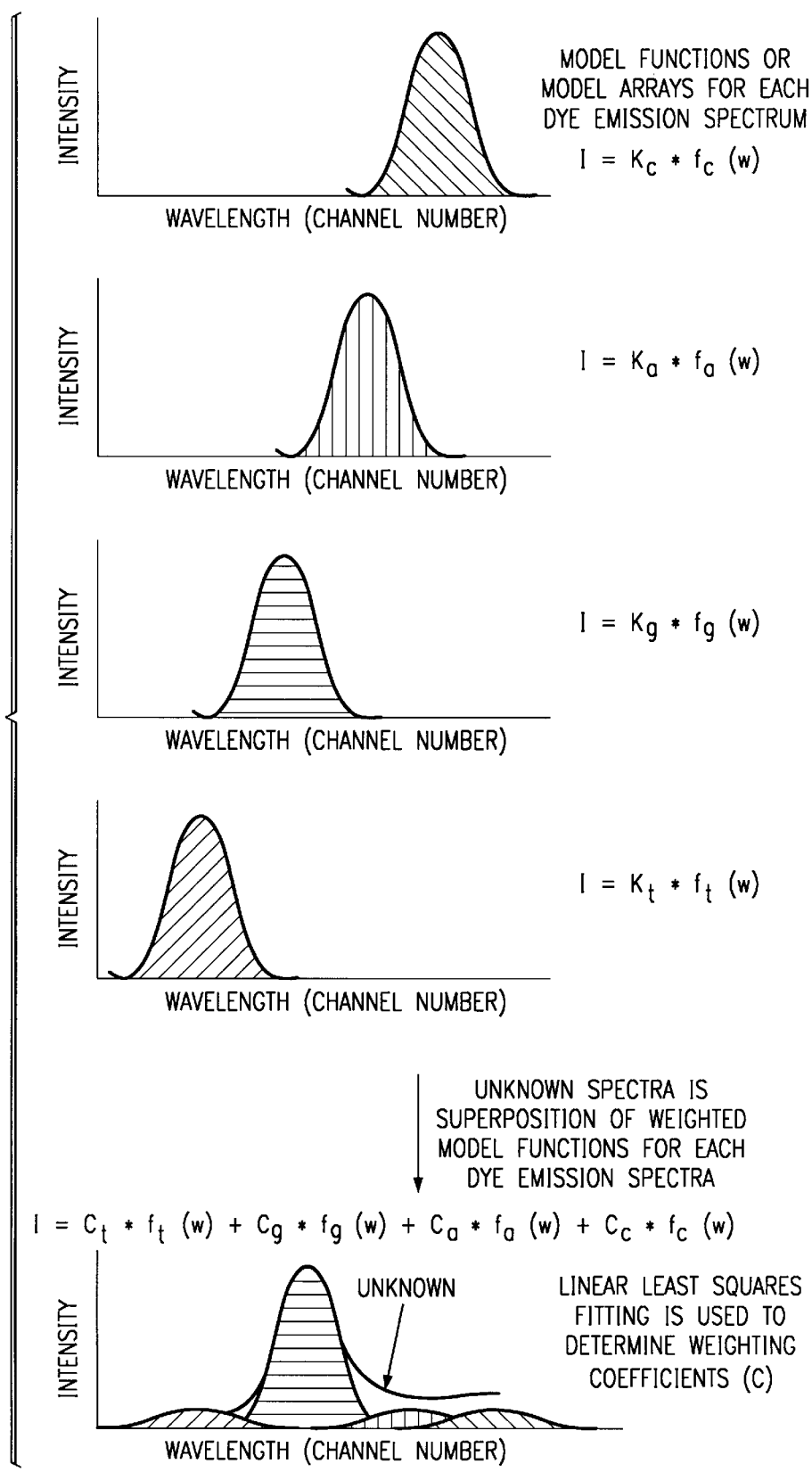
FIG. 5 is a summary of the steps involved in spectral decomposition of captured images.

FIGS. 3 through 5 show a composite of the basic steps involved in hyperspectral imaging as used by the hyperspectral slide reader 10 disclosed herein. The process begins with the capture of two-dimensional images, depicted as 60 in FIG. 3. From the captured images 60, a composite image is assembled, depicted in a display unit 36. The spectra are converted into a vertical cut in the lower two-dimensional image of a slide, depicted as 62 in FIG. 4. The upper images are space along the horizontal axis and the full spectra along the vertical axis.

FIG. 5 is a diagram showing the basic steps in spectral decomposition. Curve fitting is depicted based on the known measured dye spectra from the fluorochromes selected for staining and the light source selected. As described hereinabove, the light source can include more than one light source providing one or more wavelengths (up to the entire spectrum of light) for analysis. Model functions or model arrays are preselected from a database of dye emission spectrums, or may be captured prior to analysis from known fluorochromes having known amounts. The spectra from the unknown samples is then captured and superpositioned on the weighted model functions derived from the known dye emission spectra. The models are weighted depending on, e.g., the power of the contribution of that laser or lamp to the light source. Finally, the unknown is fit on the known emission spectrum or spectra using, e.g., linear least square analysis, which allows for computationally solving the fitting equation to minimize the residuals.

The hyperspectral slide reader 10 of the present invention is capable of the multiple fluorescence wavelength detection required expression level analysis of at least 10,000 independent samples deposited or created on slides. To deposit that many samples of a single slide, a microchemical spotting system may be used. Such systems are presently used at Stanford University, California, or from Synteni, U.S.A. Alternatively, other slide spotting systems may be built using array technologies such a photolithographic techniques and photodeprotection chemistry.

High density arrays of oligonucleotide (or other) probes are an emerging technology for research and potential clinical diagnostics. Arrays of up to 65,000 oligos, manufactured using photolithographic methods are now available commercially from Affymetrix/Hewlett Packard. These arrays are used for resequencing and expression studies via hybridization to the array. These chips currently have feature sizes of 20 micron. The present invention provides and alternative handling and data acquisition and analysis system for the analysis of biological sequence on slides.

The present invention takes advantage of slide spotter systems in conjunction with a hyperspectral reader for gene expression analysis. Specifically, hyperspectral technology has been applied to measure the expression level of all 6,217 genes (ORFs) in yeast in response to knocking-out each gene, thus creating a 6,217×6,217 array of expression results, from which the gene networks will be computed.

The slide spotter may be constructed from a Toshiba high precision/reproducibility pick and place robot with a multichannel spotting head. The robot is programmable from a teach pendant or via PC computer. Different types of print heads may be used to spot slides, e.g., a pin spotter, a microvalve/capillary spotter or a piezoelectric/capillary spotter. These provide options of increasing accuracy, complexity and risk. An ultra clean environment is maintained using a HEPA filter to pressurize robot operating volume and proper clean room practices. Microwell plates are kept cool using a surface chiller to minimize evaporation.

Specifications for a slide spotter can include a spot volume of 500 picoliters to 10 nanoliters, a total volume deposited of 500 picoliters (if used with 40 slides this requires 20 nanoliters to 400 nanoliters of volume), and a total sample prime volume of 2 microliters. A drop size for use with slide spotting may be 90 picoliters (e.g., a piezo shooter system, 0.5–1.0 nanoliters for microvalve, or 1–10 nanoliters for pin tool). The system should provide a spot reproducibility of approximately >95%. Shoot times of 6 milliseconds (piezo) to 0.1 seconds (microvalve or pin tool) may be used. Spot dimensions may be of up to about 100 microns on a slide size of, e.g., one inch×three inches. A post grid or orientation may be of 48×144 post, with a slide spot area of 0.75×2.25 inches (about 19 mm×57 mm). The distance between spots may be of about 0.19 mm/48 spots which totals 396 microns. The X-Y step size and reproducibility of a Toshiba robot is about 20.3 microns, which yields an X-Y step between spots of 396 microns/20.3 microns to give 19 spots. In one example of a slide spotter a 384-well plate may be used, with up to about 18 384-well plates kept on a chilled plate to control evaporation. In this example, the samples "on deck" or queued in the plates may be of about 6,912. Slides on deck may be, e.g., forty, if six potter pins/shooters are used per robot arm. Basic functions or steps per cycle can include: clean, aspirate, prime/verify shooter, and spot.

In operation, the hyperspectral slide reader may be used for, e.g., expression analysis. Polymerase Chain Reaction Polymerase Chain Reaction (PCR) products, cDNAs, oligonucleotides and DNA fragments have been spotted on glass as high-density hybridization targets. Fluorescently labeled cDNAs derived from cellular extracts of mRNA have achieved a dynamic range (detection limit) of 1 in 10,000 to 100,000, allowing for detection of message in low and high abundance. Many experiments to measure differential expression have been reported for yeast, Arabidopsis and human DNAs. Presently, comprehensive and concise data on quantitative analysis of gene expression are available. Use of known expression data may be used to predict and measure known expression patterns having clinical/clinical research application with unknown samples to obtain realtime expression data.

The present invention may be used with existing photochemical protocols and slide spotting technology, in conjunction with known expression levels for preselected and known genes, to optimize gene expression analysis using multiplexing of query samples by using a number of dyes and the full spectral imaging capabilities of the hyperspectral slide reader 10. The hyperspectral slide reader 10 may be used to identify the expression levels of every gene of the entire organism at one time for multiple multiplexed samples.

For example, the hyperspectral slide reader may be used for the gene networks study project of the National Institutes of Health-National Cancer Institute (NIH-NCI). The gene networks study involves the identification of yeast gene pathways by measuring the expression level of all 6,217 open reading frames (ORFs) in response to a systematic knockout of each gene (ORF). Using the hyperspectral slide reader 10, the expression level of every yeast gene in every yeast gene knockout may be determined by analyzing the expression of multiple yeast gene knockouts per slide, at a greatly reduced cost, with greater efficiency and in less time.

During expression analysis the hyperspectral slide reader 10 moves the slide 20 past the imaging optics/laser line creating exactly the same type of image. The spatial resolution in that dimension is set by the step size of the linear motion track, down to 1 micron, but will be taken such that 1536 pixels will be acquired across the dot array 50 so that a square image is generated. Use of a 500 pixel array allows the system to match spatial dimension acquired by the camera 30 in three-pixel bins. The spectra are binned in groups of 10 pixels in the spectral dimension, that is 100 pixels in the spectral dimension. This is a trade-off in acquisition/integration/analysis time and computer space sufficient to acquire a very good final cube (X, Y, wavelength) size of 50 megabytes. The image will have a 12 bit depth that will occupy 2 bytes. The image cube file can then be exported for analysis using dot blot codes already developed and implemented.

Software for analyzing high density grid hybridizations has been developed and used to analyze over 260 images containing 1536 colonies spotted on membranes. The application was developed using macros for a widely used commercial software package called IDL, a complete, integrated software environment for data analysis, visualization, and application development, made by Research Systems, Inc. (http://www.rsinc.com). The cube images are imported as either 8-bit, or 16-bit Tiff files. Key components of the analysis include spot-finding, spot-quantification, and spot addressing. The images generated by the hyperspectral slide reader 10 may be 16-bit Tiff. The 12-bit camera output will be padded to 16-bits. The slide image is analyzed for constant intensity level contours satisfying the following constraints: the contour is closed (around a spot), the enclosed area is above a minimum area threshold and below a maximum area threshold, and the spot-integrated intensity is above a minimum intensity threshold relative to background. The user is presented with software controls (widget sliders) to define the parameters min_area, max_area, and min_intensity within the user interface so that the analysis is automatic and quick. The numerical parameters that set the gradation of the contours and the coarse-graining to define the local background intensity are also adjustable. Once spots are identified and quantified, the centroid of each spot is associated with a unique grid-cell that defines the spot's address in the array. This process avoids quantification errors associated with strong signals bleeding into neighboring cells.

Figure 6:
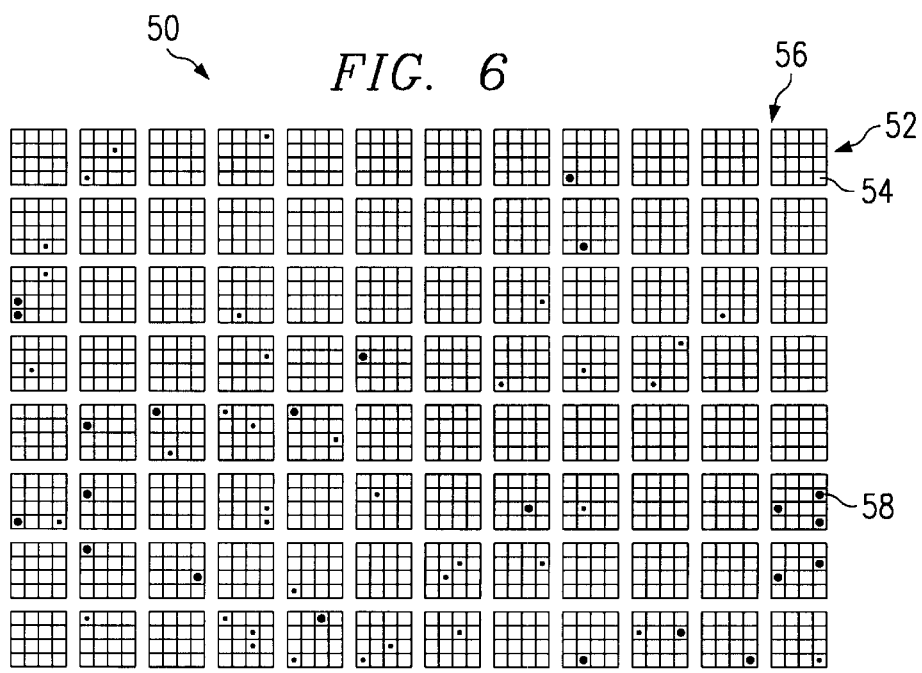
FIG. 6 is a representation of actual samples captured with an overlay of a grid format for use with the present invention.

FIG. 6 shows an example using this application to analyze an arrayed cosmid library from human chromosome 11. The filter is arranged in 96-well microplate format with four by four unit 52 for spotting, so that 16 plates, or 1536 colonies are represented in the image. Four by four units 52 are separated by streets 56, to improve the separation. The individual cells 54 that make up a four by four unit 52 can vary in size, as can the number of cells per unit 52. Furthermore, the size of the street 56 may be customized to maximize individual cell 54 size and readout parameters. In the example depicted in FIG. 3, a conventional $^{32}$P-labeled DNA probe from IRE-bubble Polymerase Chain Reaction (PCR) of a YAC spanning part of a chromosome 11 was used. Color graphics overlay the original black and white image as follows: spot-contours are yellow, the coordinate grid is blue, and grid-cells containing spot centroids 58 are red. As part of the design parameters, it is anticipated that visible imperfections will occur in the grid. These inaccuracies may be due to inaccuracy of the spotting robotics and variations in the growth morphologies of the colonies. As such, expression analysis may be carried out to determine the presence or absence of expression, as well as relative expression level.

In the present example, a positive control was first made by hybridizing the filter with radio-labeled cosmid vector to light up all the colonies, allowing construction of a master coordinate grid or dot array 50, which was then applied to each subsequent analysis of the filter and aligned using radio labeled markers. For the microarray display system described herein, high accuracy spotting robotics and in situ positive controls (using the multiple fluorescence wavelength detection of the hyperspectral slide reader 10) will allow error-free spot-addressing, thus negating the need for this module of the program that deals with grid spotting nonuniformities.

The analysis of the hyperspectral slide reader 10 data (spot pattern on the slides) should take approximately 10 minutes per slide by the software operator, 5 minutes for alignment and visual checking, and 5 minutes of processing time to produce an Excel (Microsoft Corporation, U.S.A.) readable spreadsheet output of the intensity of each color for each dot. Excel spreadsheets are used extensively because of their universality and importability into most standard databases, such as 4th Dimension or Sybase. The Excel spreadsheets will be directly imported into the analysis package used to evaluate the network of gene expressions.

Figure 7:
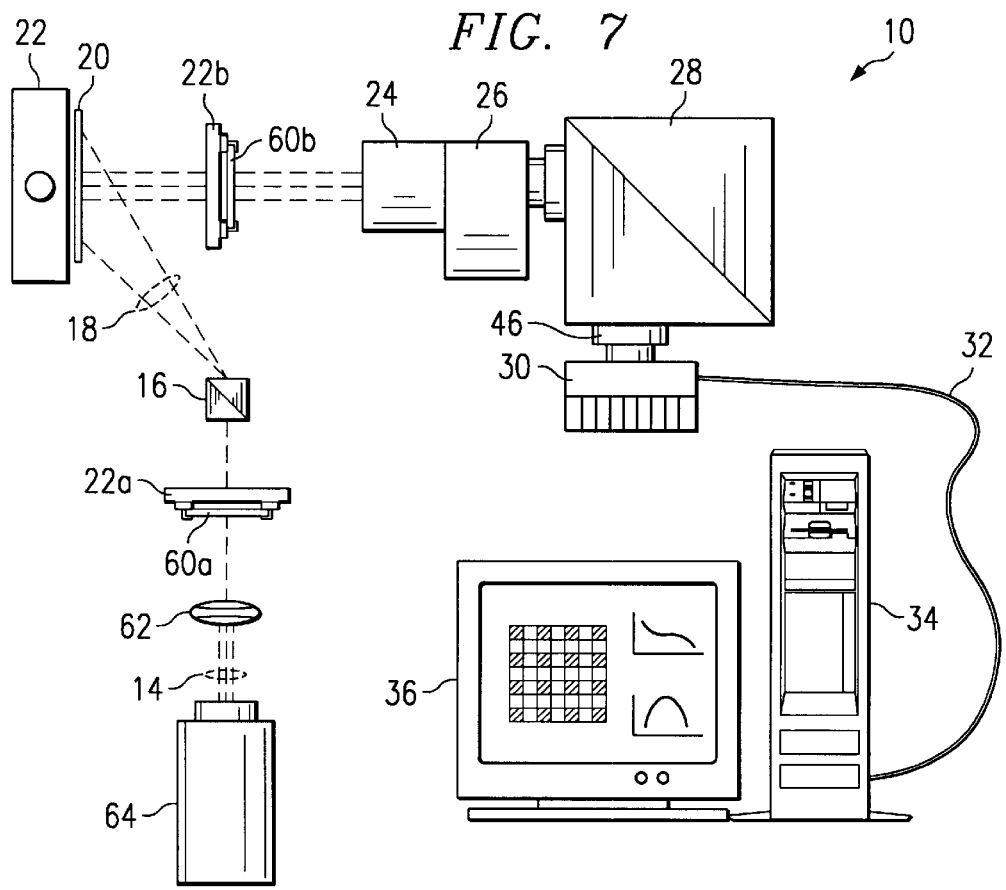
FIG. 7 is yet another diagram of a hyperspectral slide reader with independent illumination and detection system using a variable spectral filter.

FIG. 7 shows another embodiment of a hyperspectral slide reader of the present invention also generally depicted as 10. As with the previous embodiments described hereinabove in conjunction with FIG. 1, a wide spectrum light source 64, produces a light beam 14 that is spread into a light line 18 by a light line generator 62, in this case a cylindrical lens. The light line 18 strikes a slide 20 that may be moved by a slide mover 22. Alternatively, the light source 12 and light line generator 16 may not be necessary if the entire light generation process from the sample is based on chemiluminescence emitted from the sample on slide 20. Chemiluminescence for use with the invention may be as described for FIG. 1.

Figure 2:
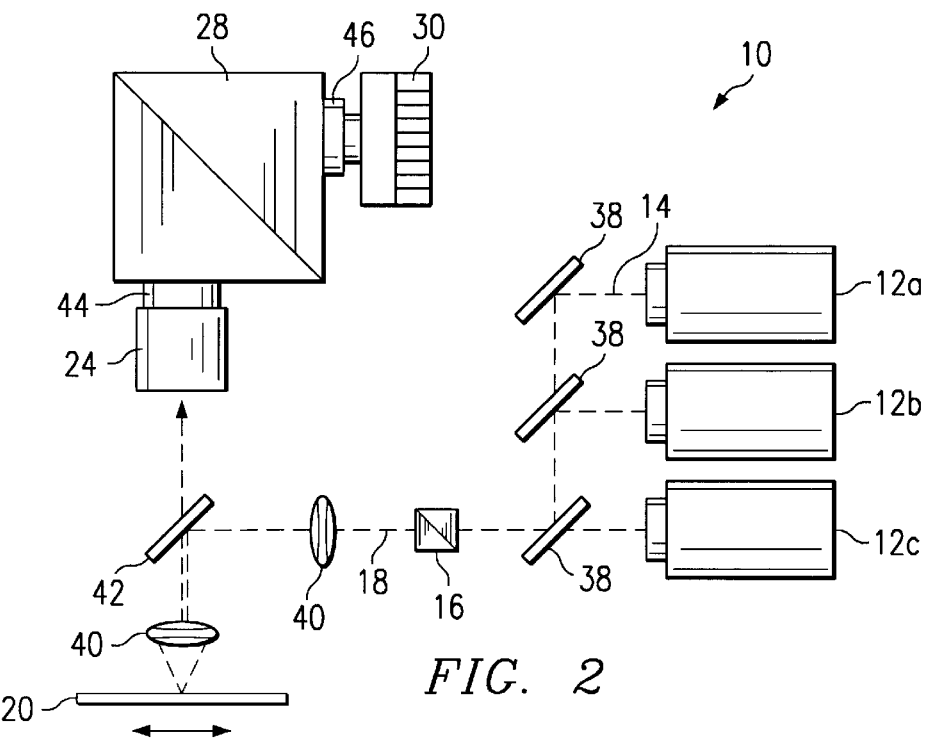
FIG. 2 is another diagram of a hyperspectral slide reader having multiple light sources with epi-fluorescence illumination and detection.
Figure 8:
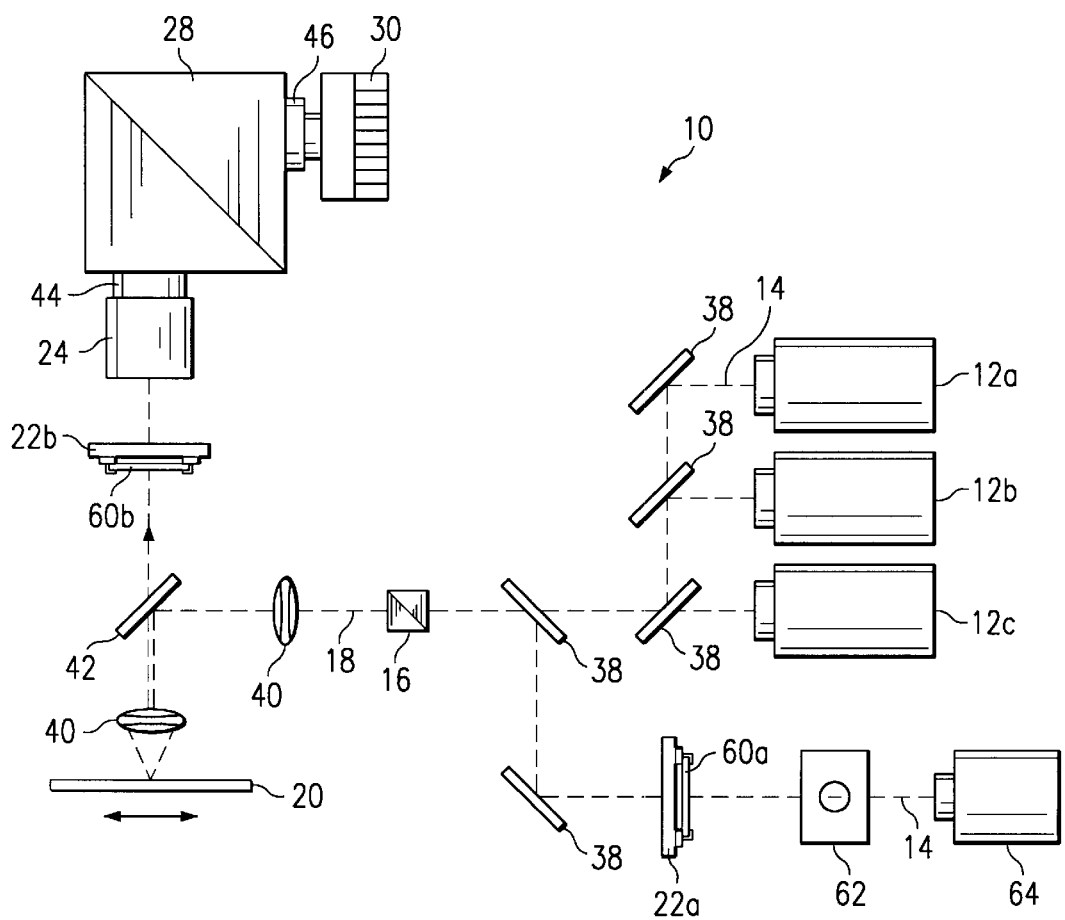
FIG. 8 is another diagram of a hyperspectral slide reader having a variable spectral filter for use with epi-fluorescence illumination and detection.

One example of a light source may include several different lasers or lamps that have different power as described for FIG. 2. These lasers are best seen in conjunction with FIG. 8, in which these lasers are numbers 12a, 12b and 12c, respectively. As with the previous embodiments described hereinabove in conjunction with FIG. 7, a wide spectrum light source 64, produces a light beam 14 that is spread into a light line 18 by a light line generator 62, in this case a light slit. Cylindrical lenses 40 are positioned to control the laser light and form a focus on the slide that may be confocal. The light line 18 is deflected into the slide 20 by a dichroic mirror 42. In this embodiment, the illumination provided by the light line 18 may be directed to the slide in either an epi-fluorescence arrangement (shown FIG. 8) or independently from the light collection optics, including illumination from above (shown in FIG. 7) or through the slide 20.

As described for FIG. 1, a number of fluorochromes may be used simultaneously for the present invention which avoids some of the limitations on single and double wavelength light source devices. Fluorochromes or dyes for use with the present invention will depend on wavelength and coupling structure compatibility and can include the specific examples discussed in relation to FIG. 1.

The embodiment shown in FIG. 7 shows a system similar to that shown in FIG. 1 with the addition of a linear variable spectral filter 60 in two configurations. An example of a variable spectral filter is a Linear Variable Spectral Density Filter (Reynard Corporation, U.S.A.). The variable spectral filter 60a is upstream of the sample. Variable spectral filter 60b, depicted downstream from the sample, but in front of the detection element may or may not be used in conjunction with variable spectral filter 60a to limit the spectral that is received by the imaging spectrometer 28. The variable spectral filter 60 is an optical device may also be described as a variable wavelength filter, in the depicted configuration in the form of a rectangular slide, that allows the passage of light at a specific wavelength at a given point along the length of the slide. A slide mover holds and controls the position of the variable spectral filter 60a or 60b. The position of the variable spectral filter 60 may also be under the control of computer 34.

In operation, the wavelength of light that passes through the variable spectral filter 60 is determined by the spatial position at which the incident beam strikes and crosses the variable spectral filter 60. This means that translation of the variable spectral filter 60 in a direction perpendicular to a beam of radiation that is striking it results in a selective filtration of the light beam such that the throughput is a scan of the wavelengths present in the incident beam for a particular linear portion of the variable spectral filter 60.

More particularly, the filters 60a and 60b are mounted on a movable stages 22a and 22b that may be identical to the one the sample slide is mounted on as described for FIG. 1. The filter-movable stage combination may also be used in either position, or in both; 22a/60a and 22b/60b. A light line generator 62, such as a light slit or a cylindrical lens, is positioned between the light source 12 and the variable spectral filter 60a such that light 14 entering the variable spectral filter 60a is a light line that is generally parallel to the variable portions of the filter. The light line strikes the variable spectral filter 60a and the output from the filter is a more narrow spectrum of light than that which enters the variable spectral filter 60a. To increase or decrease the number and specificity of the wavelength(s) of light that exit the variable spectral filter 60a, the width of the light line generated by, e.g., the light slit or cylindrical lens, is varied. By increasing the strength of the cylindrical lens, or decreasing the width of the slit, the spectral width produced by the light line generator 62 is narrowed. Conversely, by decreasing the strength of the lens, or increasing the width of the slit, the spectral width produced by the light line generator 62 is broadened.

Furthermore, two filters may be positioned in series to provide further refinement to the control of the wavelength that passes through both variable spectral filters 60. Using a variable spectral filter 60 in position 60a allows for the light line to be held in one position over the sample while the full spectrum of incident radiation is swept by moving the variable spectral filter 60. An incident radiation sweep allows for the separation of the excitation in the temporal regime of two flourescent chromophores that are very close in wavelength. This application of a linear variable filter over an infinitely broad range of wavelengths offers great advantage over traditional "drop-in" filter systems. Drop-in filter systems provide no means to scan across a wavelength spectrum. Furthermore, drop-in filter systems merely offer the possibility of discretely removing sections of the spectrum of the incident radiation. The use of a variable spectral filter 60 in position 60b allows for the tuning of the detection chain so that two flourescent chromophores that are very close in wavelength may be observed independently of one another.

In operation, a sample is affixed to a slide 20 for analysis. A light source 12 (in FIG. 7) such as a 40 mW Argon ion laser, or a combination of light sources 12a, 12b, 12c (in FIG. 8) which may be a 25 mW Argon laser, a 10 mW Diode pumped solid state laser, and 1 mW HeNe laser that have been combined into a single beam by mirrors 38, is passed through a linear variable spectral filter 60 mounted on a movable stage 22a. As depicted, the beam of light is then passed through a light line generator to produce a light line that will impinge upon the sample. Alternatively, the light line generator may be upstream from the variable spectral filter 60.

The sample may also be mounted on a movable stage that allows it to be translated relative to the light line. The linear variable spectral filter 60 allows for the illuminating light to be selectively filtered to a very narrow range of wavelengths as it strikes the surface of the filter. The nature of the variable spectral filter 60 is such that where the incident light beam or light line strikes the filter along its surface, it determines the wavelength of light that is allowed to pass through it. This filtration process effectively transforms the broadband source or sources into a continuum of single-wavelength sources that may either be swept or individually selected depending on whether the filter is kept in motion or fixed in one position to allow the passage of a single wavelength from the source. The variable spectral filter 60 may also be moved back and forth to take measurements of the sample such that the filter blocks out wavelengths that may bleach the sample in between measurements. The dual filter system also permits fine tuning of the input and output wavelength, by permitting only the input wavelength to strike the sample and only the output wavelength to exit the sample and cross the second variable spectral filter 60.

Furthermore, the combination of the movable sample stage and the movable filter stage allows the sample to be scanned by each wavelength present in the light source at each translational position on the sample before it is moved the next increment and the scanning process repeated. By using this method the excitation of the different flourescent chromophores in the sample will be separated temporally. This is a useful technique if there are different chromophores that have excitation wavelengths that are very close to one another.

The following method is an alternative that may be used with the present invention. Concurrent with the excitation of the sample may be the measurement of the resulting fluorescence. This may be accomplished by placing the variable spectral filter 60b between the sample and the detection system. The variable spectral filter 60b may be mounted on a movable stage that allows the fluorescence of the sample to be scanned in a similar manner to the way that the incident radiation may be scanned. This method permits for the resolution of fluorescence wavelengths that are very close to one another by controlling the wavelength(s) striking the sample as well as the wavelength(s) entering the detector. This ability to separate the flourescent wavelengths adds a refinement on the output side similar to the benefit achieved by the filtration of the incident beam on the excitation side. The possible need for the filters in both positions 60a and 60b derives from the fact that excitation and fluorescence wavelengths for fluorochromes are often different so that there is advantage to being able to filter the excitation spectrum and the fluorescence spectrum separately.

The selectively filtered light that passes through filter 60b then enters a focusing lens 24 before entering a light amplifier 28, which allows the signal to be more readily recorded in real time by the camera 30. The camera 30 may be connected directly to a computer 34 which may be used for data storage and manipulation as well as control of the variable spectral filters 60.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An apparatus for reading sample fluorescence from a sample on a slide, the apparatus comprising:
   a slide mover positioned to hold a slide, wherein said slide has disposed thereon a sample capable of emitting light;
   an imaging spectrometer positioned to split light emitted from said sample into a light array; and
   a camera positioned to detect said light array produced by said imaging spectrometer, wherein said camera detects said light array from said sample that has been dispersed by said imaging spectrometer to determine sample fluorescence.

2. The apparatus of claim 1, further comprising:
   at least one light source; and
   a light line generator positioned to form a light line that interacts with said sample disposed on said slide.

3. The apparatus of claim 2, wherein said light source is an argon laser, or a diode-pumped solid state laser, or a helium-neon laser or a combination thereof.

4. The apparatus of claim 2, wherein said light source is a broadband ultraviolet lamp, or a mercury lamp, or a xenon lamp or a combination thereof.

5. The apparatus of claim 1, wherein said sample on said slide is light emitting.

6. The apparatus of claim 1, wherein said imaging spectrometer is a light slit imaging spectrograph.

7. The apparatus of claim 1, wherein said camera is further defined as a charge-coupled display camera.

8. The apparatus of claim 1, further comprising an astigmatism correcting lens between said slide and said imaging spectrometer.

9. The apparatus of claim 1, wherein said slide mover is further defined as a linear motion drive slide mount.

10. The apparatus of claim 2, wherein said light source is further defined as producing a continiuum of light.

11. The apparatus of claim 10, wherein said light source producing said continiuum of light comprises an argon laser, or a diode-pumped solid state laser, or a helium-neon laser, or a broadband ultraviolet lamp, or a mercury lamp, or a zenon lamp, or a combination thereof.

12. The apparatus of claim 2, wherein said light line is further defined as comprising light produced by at least one laser or one lamp.

13. The apparatus of claim 2, wherein said light source is selected depending on the fluorochrome that is used to stain said sample on said slide.

14. The apparatus of claim 1, further comprising:
   a microchannel plate light amplifier positioned between said imaging spectrometer and said camera.

15. The apparatus of claim 1, further comprising a data acquisition system connected to said camera, wherein said data acquisition system stores and computes results based on the input acquired from said camera.

16. The apparatus of claim 1, further comprising a variable spectral filter positioned between said sample and said imaging spectrometer.

17. The apparatus of claim 2, further comprising a variable spectral filter positioned between said light source and said sample.

18. The apparatus of claim 16, wherein said variable spectral filter is positioned on a slide mover.

19. The apparatus of claim 16, wherein said variable spectral filter is a linear variable spectral slide filter.

20. An apparatus for reading sample fluorescence from a sample on a slide, the apparatus comprising:

a slide mover positioned to hold said slide;

a imaging spectrometer positioned to split light emitted from said sample into a light array;

a light amplifier positioned to amplify said light array;

a CCD camera to detect said amplified light array produced by said light amplifier, said CCD camera producing an output; and a data acquisition system connected to said CCD camera, said data acquisition system capable of storing and computing results based on the output from said CCD camera, wherein said camera detects said light array from said sample that has been dispersed by said imaging spectrometer to determine sample fluorescence.

21. The apparatus of claim 20, further comprising:

at least one light source; and a light line generator positioned to form a light line that interacts with said sample disposed on said slide.

22. The apparatus of claim 21, wherein said light source is an argon laser, or a diode-pumped solid state laser, or a helium-neon laser or a combination thereof.

23. The apparatus of claim 21, wherein said light source is a lamp.

24. The apparatus of claim 21, wherein said light source is a broadband ultraviolet lamp, or a mercury lamp, or a xenon lamp or a combination thereof.

25. The apparatus of claim 20, wherein said imaging spectrometer is a light slit imaging spectrograph.

26. The apparatus of claim 20, further comprising an astigmatism correcting lens between said slide mover and said imaging spectrometer.

27. The apparatus of claim 20, wherein said slide mover is further defined as a linear motion drive slide mount.

28. The apparatus of claim 21, wherein said light source is further defined as producing a continiuum of light.

29. The apparatus of claim 28, wherein said light source producing said continiuum of light comprises an argon laser, or a diode-pumped solid state laser, or a helium-neon laser, or a broadband ultraviolet lamp, or a mercury lamp, or a zenon lamp, or a combination thereof.

30. The apparatus of claim 20, wherein said sample is light emitting.

31. The apparatus of claim 21, wherein said light line is further defined as comprising light produced by at least one laser or one lamp or combinations thereof.

32. The apparatus of claim 21, wherein said light source is selected depending on the fluorochrome that is used to stain said sample.

33. The apparatus of claim 21, wherein said light amplifier is further defined as a microchannel plate amplifier.

34. The apparatus of claim 20, further comprising a variable spectral filter positioned between said sample and said imaging spectrometer.

35. The apparatus of claim 21, further comprising a variable spectral filter positioned between said light source and said sample.

36. The apparatus of claim 34, wherein said variable spectral filter is positioned on a slide mover.

37. The apparatus of claim 34, wherein said variable spectral filter is a linear variable spectral slide filter.

38. A method of scanning sample fluorescence on a slide in multiple wavelengths comprising the steps of:

splitting light emitted by at least one sample on said slide into a two dimensional array of light;

amplifying said array of light using a microchannel plate light amplifier; and detecting said two dimensional array of light, wherein said two dimensional array of light is representative of the emission spectra of said sample on said slide.

39. The method of claim 38, wherein said step of splitting said light into a two dimensional array is accomplished using an imaging spectrometer.

40. The method of claim 38, further comprising the step of converting said array of light into a digital format for spectral decomposition analysis.

41. The method of claim 38, wherein said step of detecting said two dimensional array of light is accomplished using a CCD camera.

42. The method of claim 38, wherein said step of detecting said two dimensional array of light is further defined as hyperspectral imaging, wherein all the emission spectra are detected at high spectral resolution by a CCD camera and used to determine the relative intensities of each fluorochrome that contributes to the output of said sample by a spectral decomposition analysis in which the signature emission spectra of each fluorochrome is compared to the complete emission spectra of said samples.

43. The method of claim 38, wherein said light on said slide is produced by a chemiluminescent reaction on said slide.

44. The method of claim 38, further comprising the steps of:

generating a light line from a light source; and illuminating said light line through at least one sample, prior to the step of splitting light emitted by at least one sample on said slide into a two dimensional array of light.

45. The method of claim 44, further comprising the steps of:

positioning a variable spectral filter such that where the light line strikes the filter along its surface it determines the wavelength of light that is allowed to pass through said filter.

46. The method of claim 44, further comprising the steps of:

positioning a variable spectral filter between said light source and said sample such that the light that strikes the sample is at a discrete wavelength.

47. The method of claim 46, wherein the variable spectral filter may be swept across the light to allow the discrete measurements in a time-dependent manner for a single wavelength of light at any given time-point.

48. The method of claim 46, wherein the variable spectral filter is positioned on a slide mover.

49. The method of claim 48, wherein the position of said variable spectral filter is controlled by a computer.

50. The method of claim 46, wherein the width of the light is varied before it strikes the variable spectral filter to control the wavelength(s) that exit the filter.

51. The method of claim 46, wherein increasing the width of the light before it strikes the variable spectral filter increases the number of wavelength(s) that exit the filter.

52. The method of claim 46, wherein decreasing the width of the light before it strikes the variable spectral filter decreases the number of wavelength(s) that exit the filter.

53. The method of claim 44, wherein said light line is generated by a light slit.

54. The method of claim 44, wherein said light line is generated by a cylindrical lens.

* * * * *